United States Patent [19]
Evers et al.

[11] Patent Number: 5,843,138
[45] Date of Patent: Dec. 1, 1998

[54] PACEMAKER SYSTEM WITH ENHANCED PROGRAMMABLE MODIFICATION CAPACITY

[75] Inventors: Xander Evers; Johannes S. van der Veen, both of Dieren; Malcolm J.S. Begemann, Velp, all of Netherlands

[73] Assignee: Vitatron Medical, B.V., Dieren, Netherlands

[21] Appl. No.: 890,435

[22] Filed: Jul. 9, 1997

[51] Int. Cl.[6] ................................................... A61N 1/37
[52] U.S. Cl. ............................................................ 607/30
[58] Field of Search ................................ 607/30, 31, 32, 607/9

[56] References Cited

U.S. PATENT DOCUMENTS 5,456,691 10/1995 Snell .......................................... 607/30
5,456,692 10/1995 Smith, Jr. et al. ........................ 607/31

OTHER PUBLICATIONS

F.H.M. Wittkampf et al., "The Importance of Software Programmable Pacemakers: In Vivo Programming of a Prototype Device," PACE, vol. 7, Nov.–Dec. 1984, Part II., pp. 1207–1212.

*Primary Examiner*—Scott M. Getzow
*Attorney, Agent, or Firm*—Woodcock Washburn Kurtz Mackiewicz & Norris, LLP

[57] ABSTRACT

A pacemaker system is provided which provides for more flexibility in re-programming of the control software, or program which is controlling an implanted pacemaker. The system comprises an external programmer device which is capable both of programming the implanted device in a conventional way, and also downloading new control software to the implanted device, subject to predetermined system conditions. All implanted devices, e.g., pacemakers within the system of the invention, share a hardware platform, and are identified as belonging to a given one of a plurality of groups, each group being characterized as providing therapy aimed at a different condition. Each pacemaker also carries type data, indicating the type of pacemaker within the group, and a set of permissions data representative of different types within the group to which it is permitted to be programmed. Upon interrogating the implanted device, the programmer determines whether the device is part of the system, what its group and type is, and whether it is able to modify the device.

16 Claims, 8 Drawing Sheets

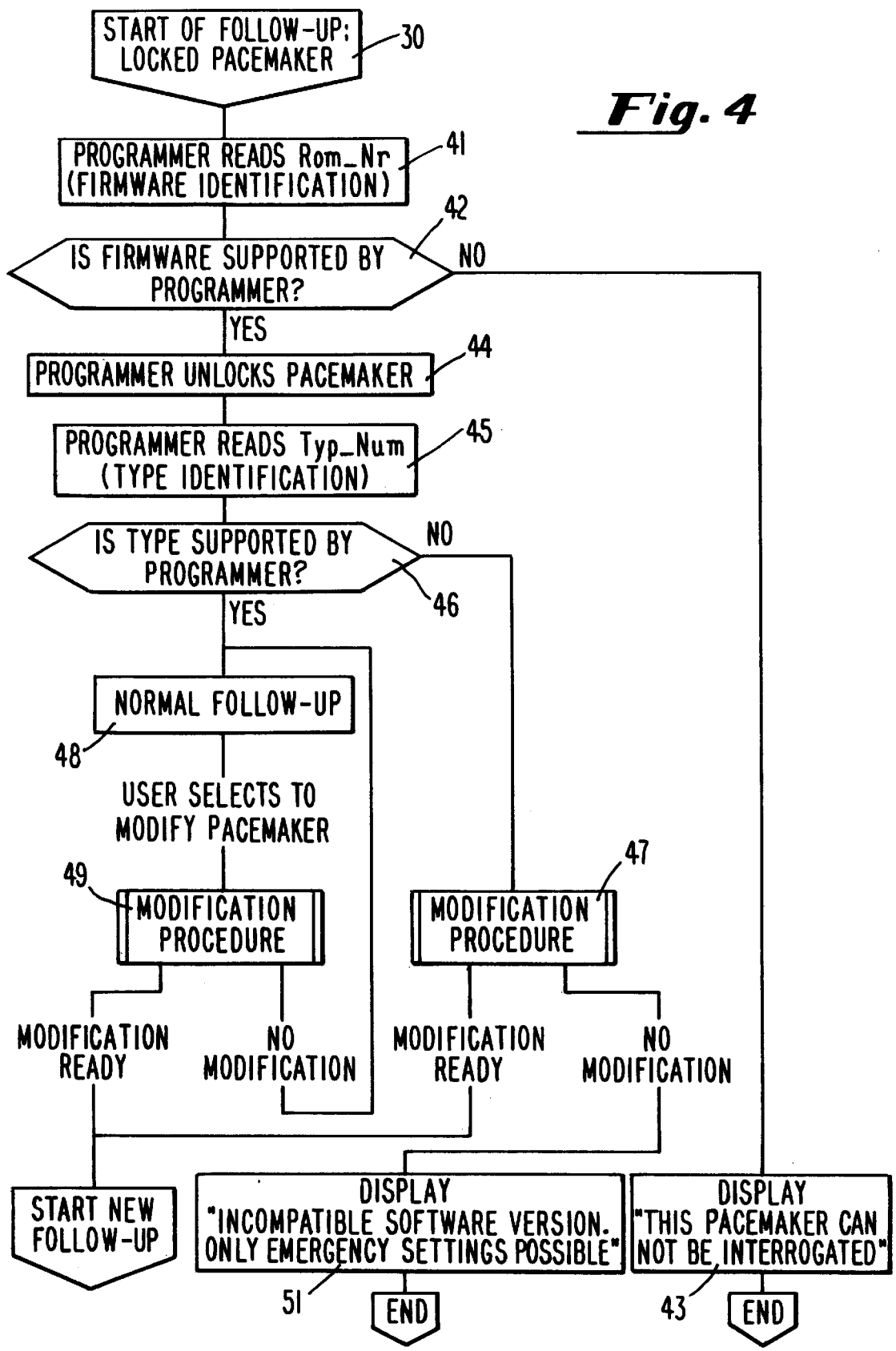

PACEMAKER SYSTEM WITH ENHANCED PROGRAMMABLE MODIFICATION CAPACITY

FIELD OF THE INVENTION

This invention lies in the field of programmable pacemaker systems and, more particularly, to systems and methods for downloading a new program into an implanted pacemaker subject to restrictions which provide security that only a program which is appropriate to the implanted pacemaker is so downloaded.

BACKGROUND OF THE INVENTION

Implantable medical devices, and in particular stimulus devices such as cardiac pacemakers, have for some time been software programmable. By software programmable, it is meant that the implanted device contains a form of microprocessor or microcomputer, and associated memory, the memory containing a control program for controlling prescribed device operations. Such programmable, or software control has become necessary with the advent of more sophisticated and complex pacemaker devices, wherein real time operation can be achieved only with microprocessor-based control. For example, with the increased use of DDD pacing, and rate responsive pacing, as well as ongoing collection of events for diagnostic purposes, exclusive hardware control simply is no longer feasible. The demands for microprocessor control led to the development of pacemakers with platforms, or main building blocks, wherein the pacemaker could be modified by the software that was downloaded into its memory. This technique enables producing different pacemaker types at the factory, or manufacturing site, by the expedient of loading the appropriate control program or programs into the pacemaker. The use of microprocessor-based pacemakers also enables a subsequent update of already implanted pacemakers, by downloading new control programs, or software, through the use of commercially available external programmer devices. Such capacity for downloading new control program software into an implanted parameter enables building a device platform which is flexible enough to be software modified in the future to adapt it for different applications and studies. For example, a pacemaker can be upgraded with new diagnostic tools and therapies to study the onset and prevention of atrial tacharrhythmias. A pacemaker implanted in a patient who was subsequently jeopardized by a different heart failure mode would have the capacity to have his implanted pacemaker modified to enable an appropriate new therapy and to carry out new diagnostic data accumulation. Of course, downloading of new software into an implanted pacemaker, i.e., using an external programmer to transmit a new control program for memory storage in the pacemaker, depends upon access to a programmer. The programmer must be capable of providing the desired software modification, and also be capable of more conventional programming the pacemaker, e.g., setting stimulus pulse parameters, rate limits, etc. Thus, it can be understood that with such technology, in the future there could be a large number of implanted pacemakers having the same hardware platform, but having been programmed differently either at the time of initial factory production or subsequently; and at the same time there might exist a large number of external programmers in use by physicians, each programmer equipped with a series of software updates depending upon the physician's access to the updates, interest in obtaining the updates, etc.

It is foreseeable that with these circumstances, there may arise a number of different situations which can produce problems. For example, a patient having an implanted pacemaker that has been upgraded in order to try a new therapy, or to obtain specific diagnostic data, may have need for re-programming of one or more pacing parameters. This could be a problem if a programmer was not available which "knew" the control program in the pacemaker, and consequently could reliably re-program the parameters. Similarly, the same patient may reach the point where it is determined that the program must be changed back to a prior and less complex control program, in which case downgrading of the pacemaker program would be required. In other situations, the pacemaker company may release an upgrade of a program, having determined that all implanted pacemakers of a particular type, i.e., with a particular control program, should be upgraded to the new control program whenever possible. In these situations, it is important that such upgrading be done automatically whenever the patient's pacemaker can be re-programed. At the same time, it is obviously important that some patients who have pacemakers for treating a first type of cardiac problem not receive program modifications designed to treat an unrelated, or second type of problem.

While the prior art has disclosed modifying control programs in implanted pacemakers, using external programmers and telemetric transmission, there remains a need for a system which ensures reliable control program modification, i.e., upgrading or downgrading, so that whatever the patient's circumstance, there is overall control over the allowed program changes. The prior art shows the ability to choose a control program from different program modules, thereby providing flexibility in the programmed software that is downloaded to a pacemaker. See U.S. Pat. No. 5,456,691. Likewise, the prior art shows the general technique of interrogating an implanted pacemaker to determine its model, and on the basis of that information, determining whether the program can be changed. See U.S. Pat. No. 5,456,692. See also the article by Wittkampf et al., November–December 1984,Part 2, PACE, Vol. 7, disclosing a programmable system where the programmer can recognize different pacemaker models, and carry out programing of the pacemaker as a function of the model. However, there remains a need for a system for controlling the program changes that could be made to any implanted pacemaker. Such a control system cannot depend exclusively on information in the programmer, since the programmer may or may not have all of the information necessary to accurately determine whether the implanted pacemaker can be upgraded with a specific new program, or downgraded to a program that is available through the programmer. Consequently, it is a primary object of this invention to provide a program modification system for use with implanted medical devices, and particularly, pacemakers, which reliably controls what changes can be made in the control program or programs stored in the implanted device.

SUMMARY OF THE INVENTION

In accordance with the above object, there is provided an implantable device system, preferably a cardiac pacemaker system, having two-way telemetric capability between an implanted pacemaker and external programmer unit. The pacemaker suitably has memory for storing a control program, and also stores data representative of a predetermined group of pacemaker types, and data representative of the specific pacemaker type according to the control program stored in the pacemaker memory. Within each defined group, the different pacemaker types are ranked in a hierarchy, from lowest to highest. Each implantable pacemaker stores permissions data representative of the model types within its group to which it can be programmed. The external programmer can receive new program releases, i.e., updated control programs, and as memory for storing a plurality of control programs corresponding to pacemaker different types, the different pacemaker types falling in one or more different groups. The programmer is software controlled to interrogate the implanted pacemaker, determine its group, type and permissions, and allows modification, i.e., upgrading or downgrading of the control program as a function of the pacemaker data and the program types that it can support.

In a first specific embodiment, the programmer of the system of this invention provides the user with an option, suitably indicated by a visual display, of whether to modify the pacemaker by downloading a different program. More specifically, in a situation where the programmer cannot support the pacemaker, i.e., cannot provide re-programming of pacemaker parameters for that particular type, the user is presented with the option of downgrading the pacemaker to a different type which is supported by the programmer being used. In another specific embodiment, the programmer is supplied with a newly released program which constitutes an improved version of a prior release program corresponding to a predetermined pacemaker type. Upon communication with the pacemaker, if the programmer finds that the pacemaker is using the prior release program, an automatic transfer is made whereby the programmer downloads the new program to replace the old program, and adjusts the pacemaker permissions data accordingly.

BRIEF DESCRIPTION OF THE DRAWINGS

FIG. 4 is a more detailed flow diagram showing the steps taken in interrogating the implanted pacemaker with a programmer, modification and follow-up.

DESCRIPTION OF THE PREFERRED EMBODIMENTS

Figure 1:
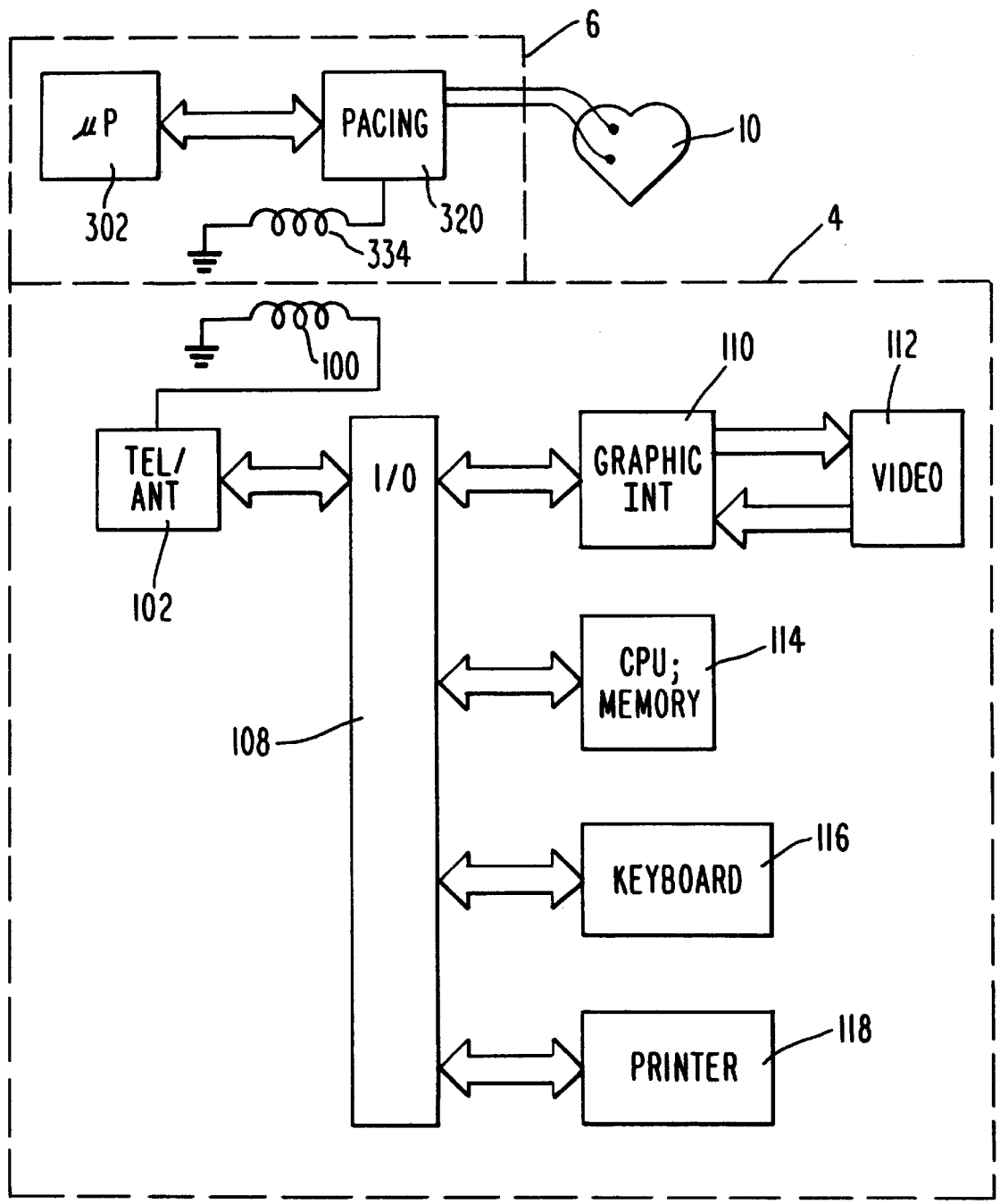
FIG. 1 is a block diagram illustrating a programmable pacing system having an external programmer and an implantable pacemaker, with telecommunications capability between the programmer and the pacemaker.

In the system of this invention, a series of devices, e.g., pacemakers are provided which are based on a common hardware platform, and are flexibly software modifiable. By modifiable, it is meant that the control program can be changed, either upgrading or downgrading the program to increase or decrease the pacemaker sophistication and capability. Thus, a common hardware platform, including microprocessor and associated memory, and conventional digital controller and timer circuitry, are provided. Different groups of pacemakers, each group using the same hardware platform, are structured to provide different therapies. Thus, for example, a first group of pacemakers may be designed specifically for treating atrial fibrillation (AF), a second group for treating heart failure (HF), etc. An external programmer utilizes information about the modification group to determine to which products, or pacemaker types, an implanted pacemaker may be modified. In this way, it is possible to control modification of an implanted pacemaker to a specific product and type only if the device is to be included in a certain study, and thus has been placed in a predetermined group. When a new product becomes available, with corresponding new software in a new programmer release, the pacemakers of some modification groups will receive permission to be modified to receive the new software, while other pacemakers will not. For example, a series of pacemakers within this invention may, at a given time, consist of six products, and four modification groups. Group A (comprising AF types) may include types 0, 1, 2 and 3; Group B may include types 0 and 4; Group C, types 0 and 5; and Group D, limited to type 1. Any pacemaker in Group A can be modified to one of the other AF types in the groups, but cannot be modified to type 4 (which may be an HF type) or to type 5. The pacemaker in Group D is to remain programmed as it was programmed at the factory and cannot be modified.

Each pacemaker has stored in memory the following data, pertinent to the modification procedure of this invention:

ROM_Nr: firmware identification

Typ_Num: type identification

Group_Id: group identification

Permissions data: 2 bytes (16 bits), each bit representing a possible pacemaker type; a 1 indicates that the type is permitted and a 0 indicates that the type is not permitted, i.e., the pacemaker cannot be modified to such type.

The following represents a programmer with a software release which supports the above illustrated series of six products and four modification groups:

| | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| Group A | 0 | 0 | 0 | 0 | 0 | 0 | 0 | 0 | 0 | 0 | 0 | 0 | 1 | 1 | 1 | 1 |

| | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| Group B | 0 | 0 | 0 | 0 | 0 | 0 | 0 | 0 | 0 | 0 | 0 | 1 | 0 | 0 | 0 | 1 |

-continued

| | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| Group C | 0 | 0 | 0 | 0 | 0 | 0 | 0 | 0 | 0 | 0 | 1 | 0 | 0 | 0 | 0 | 1 |

| | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| Group D | 0 | 0 | 0 | 0 | 0 | 0 | 0 | 0 | 0 | 0 | 0 | 0 | 0 | 0 | 1 | 0 |

The following represents an implantable device which is programmed to Group A, Type 1, and is permitted to be modified to any one of Types 0, 1, 2 and 3:

Group: A
Type: 1
Permission

| 0 | 0 | 0 | 0 | 0 | 0 | 0 | 0 | 0 | 0 | 0 | 0 | 1 | 1 | 1 | 1 |
|---|---|---|---|---|---|---|---|---|---|---|---|---|---|---|---|

Referring now to FIG. 1, a pacemaker 6 is illustrated in block diagram form, coupled to a human heart 10. Also shown is an external programmer/display apparatus 4, of a type commercially available for programming multi-programmable implantable pacemakers. Within the housing of the pacemaker there is located pacing circuitry 320, which includes circuitry performing all of the basic timing, stimulation and sensing functions of a cardiac pacemaker, and a microprocessor circuit 302, which controls the timing intervals provided by the pacing circuitry 320 and performs other logic functions. Pacing circuitry 320 also includes a bidirectional telemetry circuit coupled to an antenna 334, allowing transmission of information from external programmer 4 to pacemaker 6, and allowing transmission of information from the pacemaker 6 to the programmer 4, corresponding to telemetry and programming systems presently available. The transmission of data from the programmer to the pacemaker may consist of modifying pacing parameters, or may constitute downloading of a new program to be stored with microprocessor 302, for controlling pacemaker functions. Data transmission from pacemaker 6 to programmer 4 may include data representative of the pacemaker, as set forth above, and may also include diagnostic data which has been obtained and stored by the pacemaker.

Programmer 4, which is used by the physician, includes a corresponding antenna 100 for communicating with the pacemaker, the antenna being coupled to a telemetry/antenna driver circuit 102 which serves to demodulate telemetry signals received from antenna 334 of the pacemaker, and to apply them in parallel or serial digital format to input/output (I/O) unit 108, where they in turn may be applied to a video monitor 112 via graphic interface 110, and/or provided to central processing unit and memory 114, and/or printer 118. Unit 114 includes a microprocessor for controlling operation of the programmer/display apparatus, and is responsive to entered commands via keyboard 116, for controlling programming signals sent to the pacemaker, as well as for controlling operation of the video display 112 and printer 118. Unit 114 contains suitable memory for storing a plurality of software programs, e.g., control programs corresponding to different pacemaker types as discussed above.

Figure 2:
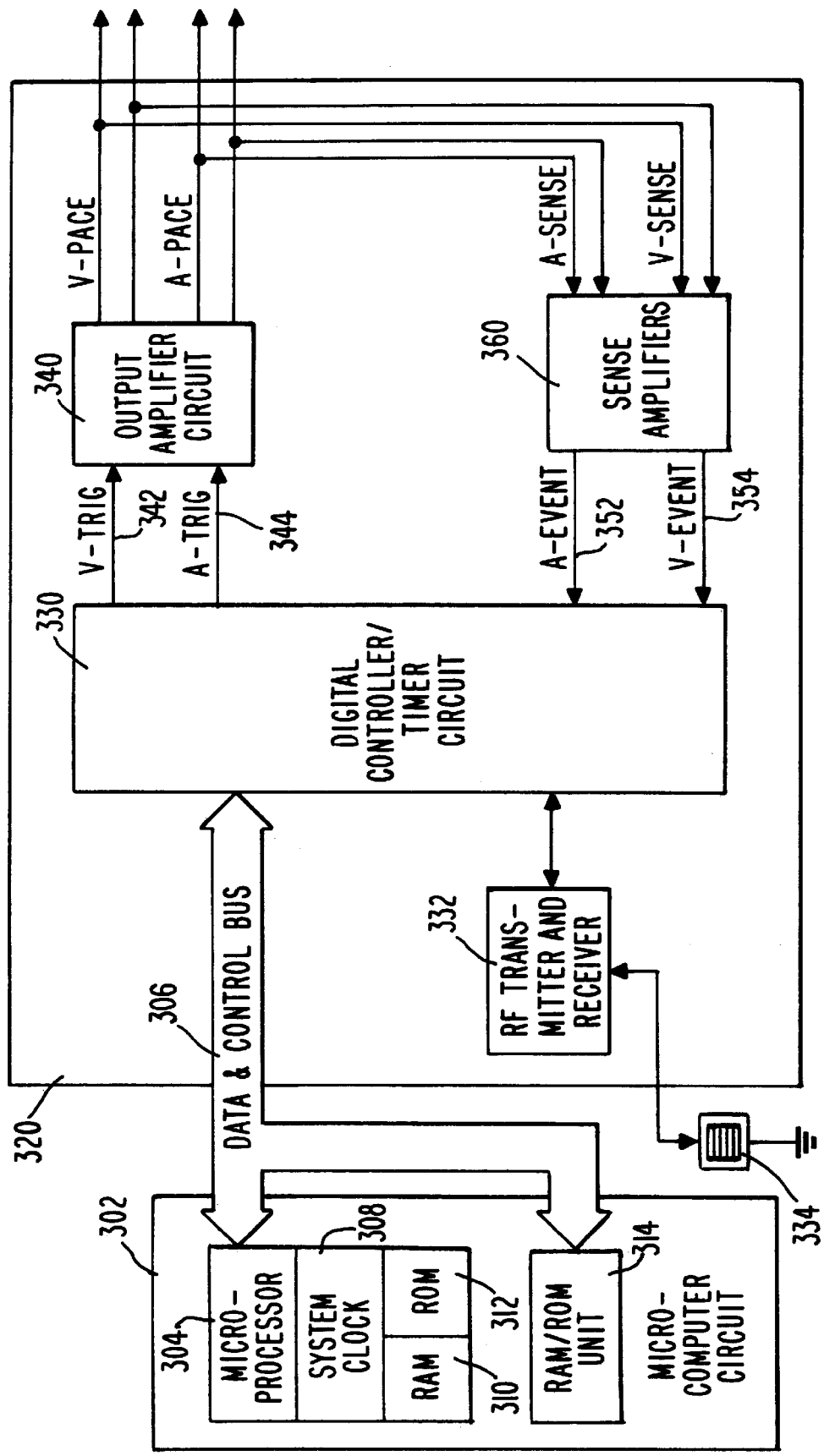
FIG. 2 is a block diagram showing the primary components of a implantable pacemaker in accordance with this invention.

FIG. 2 is a block functional diagram of the pacemaker 6 illustrated in FIG. 1. The pacemaker is divided schematically into a microcomputer circuit 302 and a pacing circuit 320. The block diagram of FIG. 2 is representative of a dual chamber pacemaker, and accordingly pulse generator circuit 340 includes a ventricular pulse generator circuit coupled to the heart by a pair of V-pace output lines as well as an atrial pulse generator circuit coupled to the heart by means of atrial lines designated A-pace. Also represented at 360 are atrial and ventricular sense amplifiers. The output circuit 340 and sense amplifier circuits 360 may contain pulse generators and sense amplifiers corresponding to any of those presently employed in modern pacemakers. Control of timing and other functions within the pacemaker circuit is provided by digital controller/timer circuit 330, which includes a set of timers and associated logic. Digital controller/timer circuit 330 defines the pacing interval of the device, which may take the form of an A—A escape interval initiated on atrial sensing or pacing and triggering atrial pacing at the expiration thereof, or may take the form of a V—V interval initiated on ventricular sensing or pacing and triggering ventricular pulse pacing at the expiration thereof. Digital controller/timer circuit 330 similarly defines the A-V escape interval for a dual chamber pacemaker providing synchronous pacing. The specific values of the interval defined are controlled by the microcomputer circuit 302 by means of data and control bus 306. Sensed atrial depolarizations are communicated to the digital controller/timer circuit 330 on A-event line 352, ventricular depolarizations are communicated to digital control/timer circuit 330 on V-event line 354. In order to trigger generation of a ventricular pacing pulse, digital controller/timer circuit 330 generates a trigger signal on V trig line 342; similarly, in order to trigger an atrial pacing pulse, digital controller/timer circuit 330 generates a trigger pulse on A-trig line 344.

Transmission to and from the external programmer 4 is accomplished by means of antenna 344 and associated RF transmitter and receiver 322, which serves both to demodulate received downlink telemetry and to transmit uplink telemetry, all in a well-known manner. Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308, and RAM circuits illustrated at 310 and 312. In addition, circuit 302 may include a separate RAM/ROM chip 314.

Figure 3:
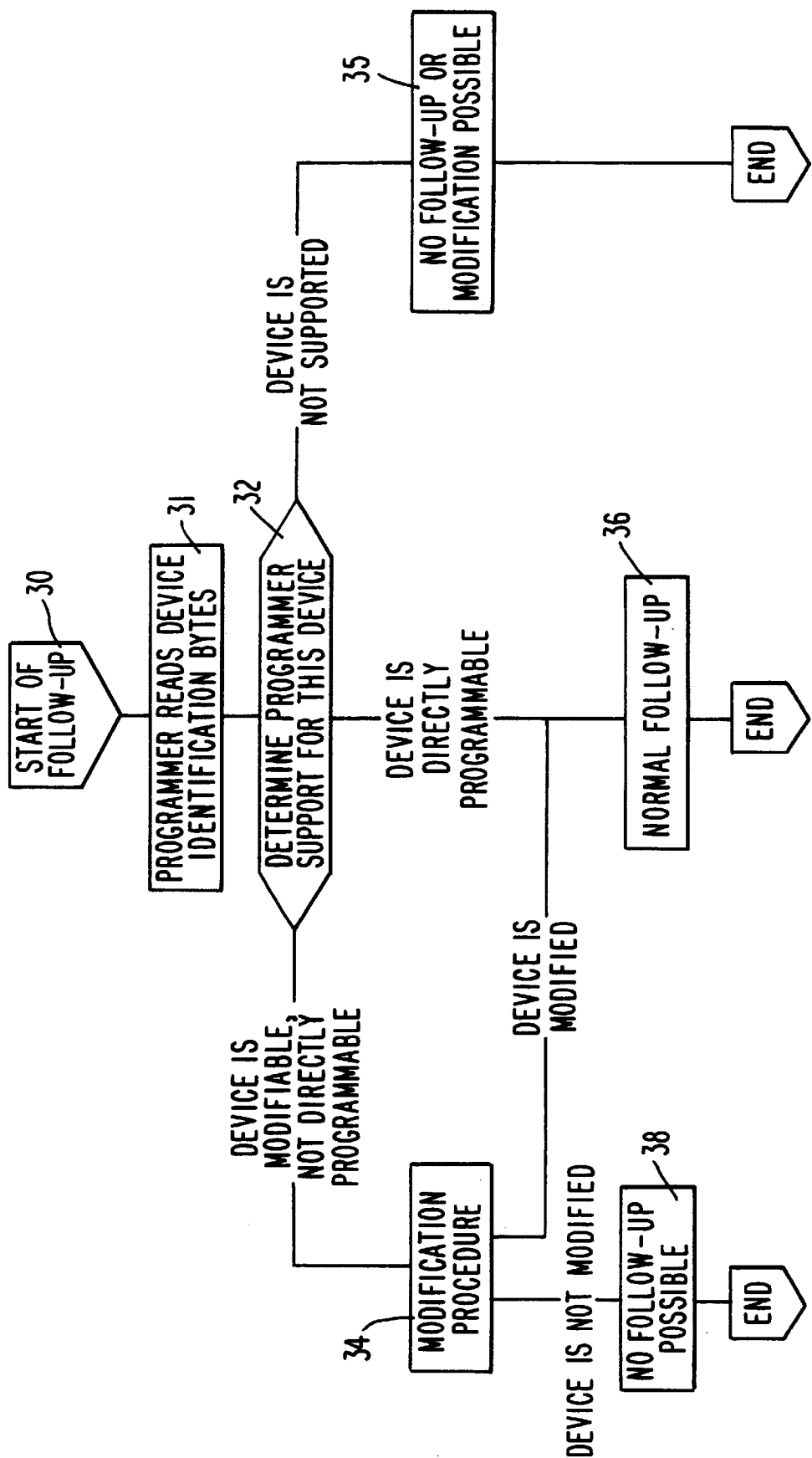
FIG. 3 is a flow diagram illustrating the principle of this invention.

Referring now to FIG. 3, there is shown a flow diagram which illustrates the principle of the invention. The physician starts patient follow-up, using the external programmer, as illustrated at 30. At 31, the programmer reads the device identification bytes, so as to obtain the pertinent information regarding the implanted pacemaker. At 32, the device identification data is compared to the programmer software, to determine whether the programmer can support this particular device. If no, as indicated at 35, no further follow-up or modification is possible. The device may be directly programmable, without modification, in which case the normal follow-up is undertaken at 36, e.g., the physician may reprogram certain basic parameters. If the device is not directly programmable but modifiable, the programmer goes to the modification procedures indicated at 34. As seen in more detail in connection with FIGS. 5A and 5B, the physician may, in some circumstances, choose to modify or not modify. If the choice is to modify, the modification procedure is suitably followed by the normal follow-up as indicated at block 36; if the choice is not to modify, no follow-up is possible, as shown at block 38.

Referring now to FIG. 4, there is shown a more detailed flow diagram of the procedure of this invention whereby the programmer determines the circumstances under which an implanted pacemaker can be or must be program modified. At 30, follow-up is started, with the pacemaker locked, i.e., it is in a fixed mode during programming. At 41, the programmer interrogates the pacemaker and reads the ROM_Nr, to get an identification of the pacemaker firmware. At 42, it is determined whether the firmware is supported by the programmer, i.e., does the pacemaker have a hardware platform compatible with this programmer 48. If no, the procedure exits as indicated at 43, providing a display to the effect that the pacemaker cannot be interrogated. However, if the firmware is supported by the programmer, the system proceeds to block 44, and unlocks the pacemaker. At 45, the programmer reads the Typ_Num, to get an identification of the pacemaker type. At 46, it is determined whether the type is supported by the programmer. If yes, the next step, as shown at 48, is normal follow-up by the physician. Note that this is situation where the pacemaker can now be directly programmed. If, as part of this follow-up, the user selects the modification procedure, then at 49 the modification is undertaken. If no modification is possible, the process loops back to normal follow-up at 48. If modification is undertaken, the physician then starts a new follow-up, i.e., the newly modified pacemaker is now programmed. Returning to 46, if the pacemaker is a type not supported by the programmer, then a modification procedure routine is entered, as indicated at block 47. This procedure may result in no modification allowed, in which case a display is provided to the physician as indicated at 51, to the effect that the pacemaker has an incompatible software version, and only emergency settings are possible.

Figure 5A:
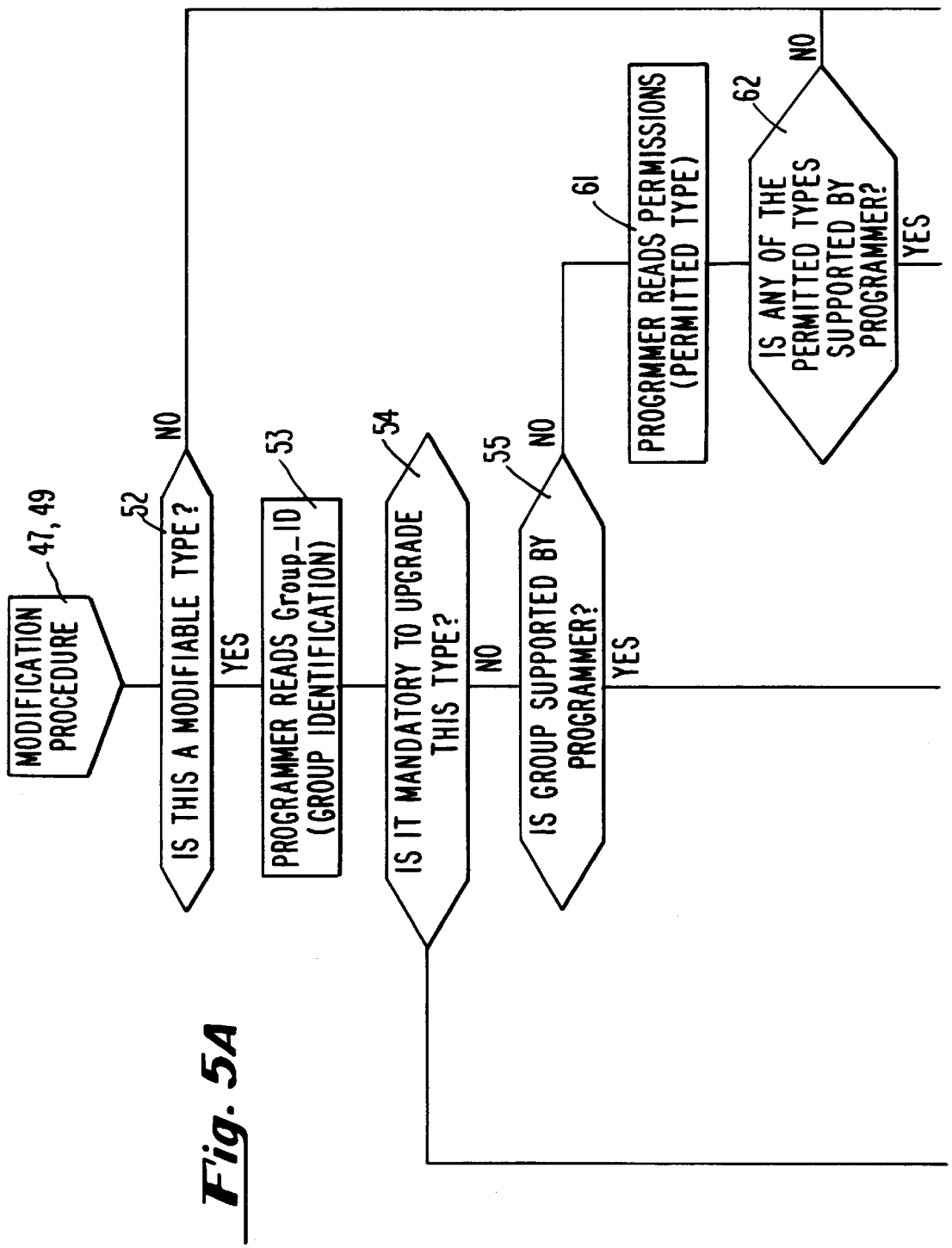
FIGS. 5A and 5B combined constitute a flow diagram showing detailed steps of the modification procedure carried out in accordance with this invention.
Figure 5B:
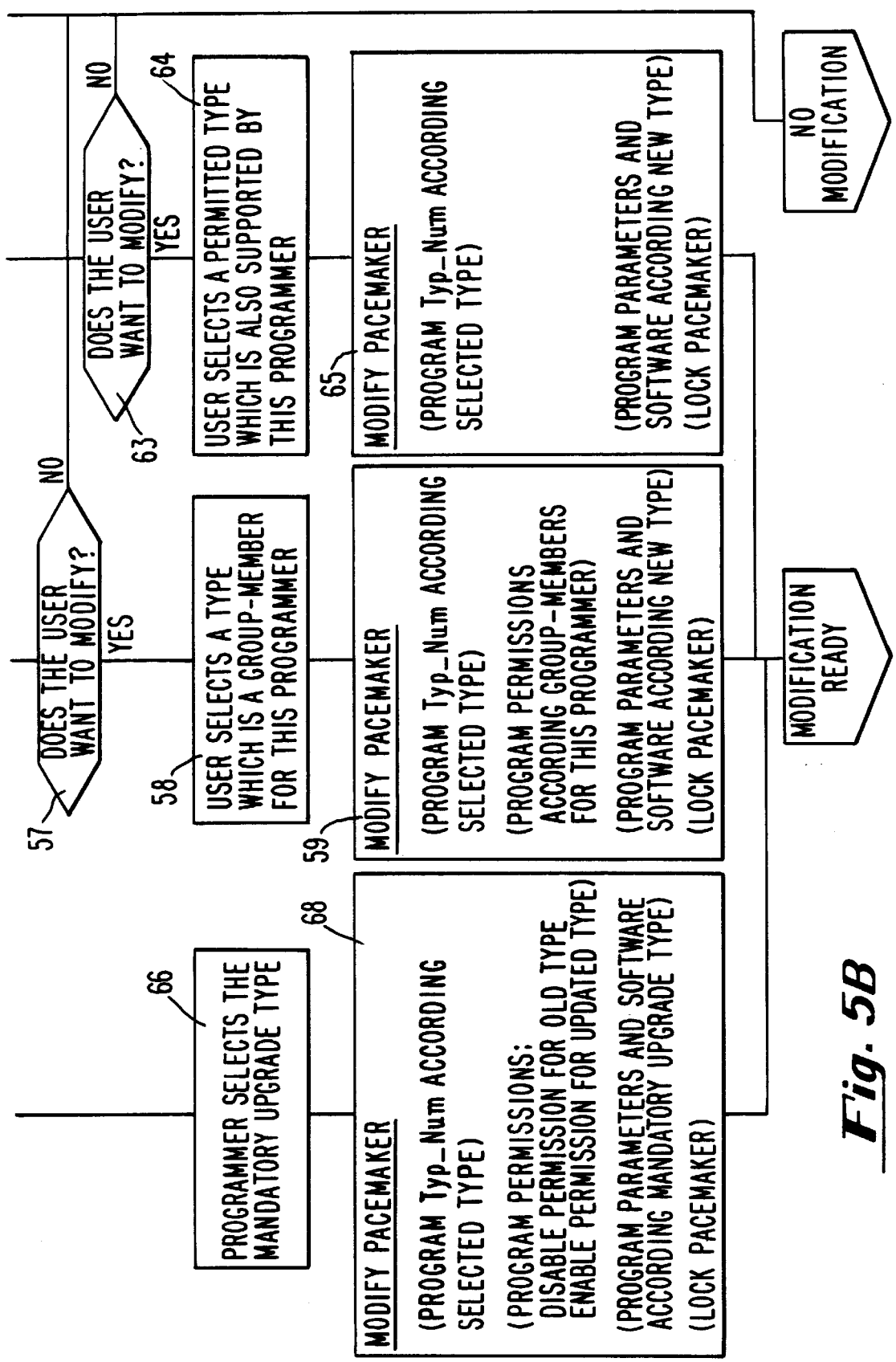

Referring now to FIGS. 5A and 5B, there is shown a more detailed flow diagram representing the modification procedure 47, 49. At 52, it is determined whether the pacemaker is modifiable type, i.e., is it a type which is part of the overall series of pacemakers adapted for modification? If yes, at 53 the programmer reads the Group_ID. After this, at 54 an initial determination is made as to whether it mandatory to upgrade this type. As discussed further below, the program version which has been stored in an implantable pacemaker type may be found to have a bug, or for any reason it may be deemed required to upgrade the program. If yes, then at block 66 the programmer automatically selects the mandatory upgrade type, and at 68 the pacemaker is modified by downloading the software corresponding to the upgrade type. As indicated at 68, this involves programming a new Typ_Num according to the selected type; changing the program permissions, e.g., disabling the permission for the old type and enabling the permission for the updated type; and programming parameters and software according to the upgrade type.

Returning to block 54, if there is no mandatory upgrade, at 55 it is determined whether the group is supported by the programmer. If yes, the routine goes to 57 and determines whether the user wants to modify the pacemaker. If yes, at 58 the user selects a type which is group member, and at 59 the pacemaker is modified accordingly. This includes programming the new Type_Num according to the selected type; re-programming the permissions according to the group members for this programmer; and programming parameters and software according to the new type.

Returning to block 55, if the group is not supported by the programmer, at 61 the programmer reads the permissions data, to determine what types are permitted. Then, at 62, it is determined if any of the permitted types are supported by the programmer in use. If yes, the user is given an option to modify the pacemaker, as indicated at 63. If this option is chosen, then at 64 the user selects a permitted type which is also supported by the programmer. At 65, the pacemaker is modified accordingly, including re-programming the Type_Num according to the selected type, and programming parameters and software according to the newly selected type.

Figures 6A, 6B:
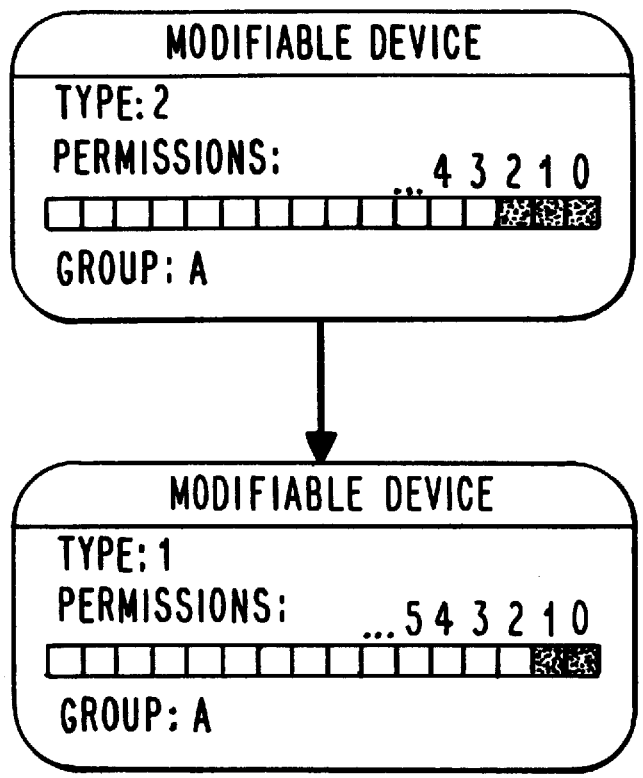
FIG. 6A is a representation of the programmer software for supporting a first combination of pacemaker types.
FIG. 6B is an illustration of changing the permissions data in an implanted pacemaker in accordance with a downgrading modification.

A specific application of the system of this invention is where a pacemaker of a relatively new type, i.e., with a late release control program, is interrogated by a programmer which does not have software to support the new type pacemaker. In this situation, the pacemaker is not directly programmable. However, in the system of this invention, the user is given an option to downgrade the pacemaker to a lower, or earlier type, after which the pacemaker can be programmed. As an example, and referring to FIGS. 6A and 6B, the situation is presented where the pacemaker is of Group A, Type 2; and Group A contains Types 0, 1 and 2. Thus, as seen in FIG. 6B, the implanted pacemaker is permitted to be modified to any one of Types 0, 1 and 2. However, while the programmer supports Group A, it only supports Types 0 and 1, and cannot support Type 2. As indicated in FIG. 6A, the programmer has software permitting it to program types 0 and 1 for Group A, and 0 and 4 for Group B (type 0 is common to both groups). In this situation, and referring first generally to FIG. 3, when a physician attempts to program the implanted device, it is determined that the device is modifiable. Referring to the more detailed flow diagram of FIG. 4, at 42 it is determined that the firmware is supported by the programmer, but at 46 it is determined that the specific type is not. Subsequently, the pacemaker goes to modification procedure block 47 Referring to FIG. 5, the detailed flow diagram of the modification block, in 52 it is determined that the implanted pacemaker is a modifiable type. At 54, it is then determined that it is not mandatory to upgrade. At 55 it is determined that the group is supported, and the permissions data loaded into the pacemaker are read at 61. After determining that there are types supported by the programmer (Types 0 and 1), the user is given the option at 63 to modify. Assuming that the user wants to modify, the new type is selected at 64, and the pacemaker is modified at 65. Note that only permissions for Types 0 and 1 are programmed into the pacemaker, i.e., it is then limited to types 0 and 1. Following this, the programmer signals that modification is ready, and the physician can proceed to restart follow-up if desired.

Figure 7A:
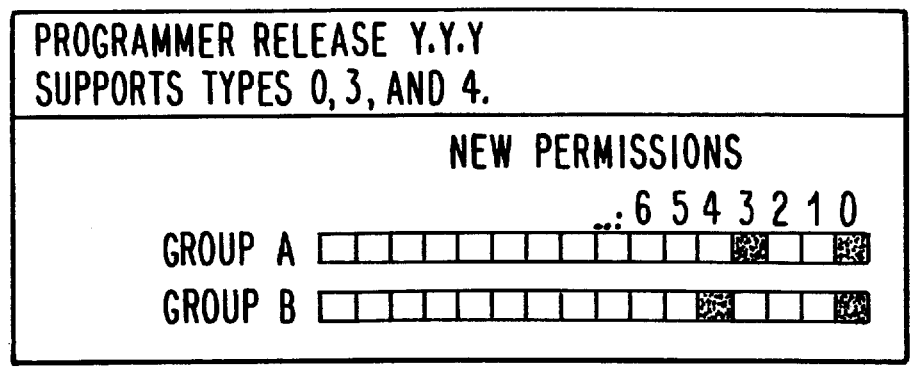
FIG. 7A is a representation of the programmer software for supporting a second combination of pacemaker types.
Figure 7B:
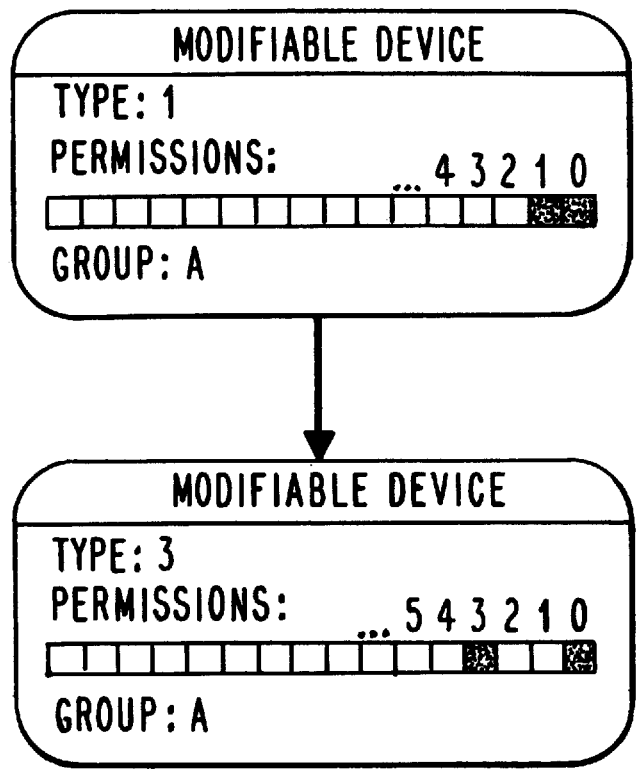
FIG. 7B is a representation of the change in permissions data in an implanted pacemaker in the mandatory upgrading modification in accordance with this invention.

Referring now to FIGS. 7A and 7B, there is shown a second set of circumstances, or scenario, where a mandatory upgrade is performed. As stated previously, an upgrade can be made mandatory where it is determined that an existing program either has a deficiency, and thus must be replaced by a corrected program, or a new program has been released which, for one reason or another, is sufficiently more advantageous so as to require upgrading. The example of FIGS. 7A and 7B illustrates a situation where a problem has been found in the program of Type 1 pacemakers, and it has been determined that all such pacemakers should be modified to Type 3, i.e., the stored program should be replaced with the latest release corresponding to Type 3. The pacemaker is in Group A, and the programmer supports Group A, and specifically supports Types 0 and 3. The task is to remove the Type 1 program and upgrade the pacemaker with the program for Type 3.

Reverting to FIGS. 3–5, in the general principle scheme as illustrated in FIG. 3, there is a determination that the device is modifiable. Referring to the detail of FIG. 4, it is determined that the firmware is supported, but the type is not supported, following which the programmer goes to the modification procedure. As indicated at FIG. 5A, after it is determined that the pacemaker is a modifiable type, it is determined at 54 that this is a mandatory upgrade, i.e., the Type 1 software must be replaced with Type 3 software. As is illustrated, the user has no choice; the programmer goes to step 66, selects the mandatory upgrade type, and at 68 proceeds to modify the pacemaker. The modification includes disabling Type 1, and enabling Type 3 in the permissions data stored in the pacemaker.

In certain situations, in accordance with this invention, the user may voluntarily modify the implanted pacemaker. For example, assume that a pacemaker belongs to Group A, and its type is 1; and that the programmer supports Types 0, 1 and 2 of Group A. In this situation, he programmer determines that the firmware is supported and the type is supported, and proceeds to normal follow-up. Referring to FIG. 5, at 52 the pacemaker is found to be modifiable, and at 54 it is found that it is not mandatory to upgrade. At 55, it is found that the group is supported by the programmer, and at 57 the user exercises the option to modify. The user then chooses the desired type, the choice being limited to a group member supported by this programmer. In another foreseeable scenario, a patient with a pacer of a type in a first group appears in a hospital where the programmer supports only groups from a second type. For example, the patient may be part of an AF study, for example, Group A, whereas the programmer is designed for pacemakers implanted in patients with heart failure, corresponding to Group B. In this case, the pacer is in Group A, and assume that its type is Type 2. Its permissions are Types 0, 1 and 2. The programmer supports only Group B, but Group B includes Type 0, a basic type to which all pacemakers in this series are modifiable. Consequently, in the modification procedure, it is determined that the pacemaker is a modifiable type; it is not mandatory to upgrade; the group is not supported, but there is one permitted type supported, i.e., Type 0. At this point, if the user wants to modify, the pacemaker can be modified only to Type 0. If this is done, the permissions data would not be changed.

Note that in a circumstance where the firmware is not supported, i.e., the ROM_Nr of the pacemaker is unknown by the programmer, then no follow-up is possible. Likewise, if the firmware is supported but the type is not supported, and the type is not a modifiable one, then again no modification or follow-up is possible; only emergency settings can be made. Likewise, if the firmware is supported, the type is not supported, the type is a modifiable type, but there is no type in the permissions data which is also supported by the programmer, then no modification or follow-up is possible.

Accordingly, there is has been disclosed a system and method for modifying pacemakers that belong to a defined series, whereby controlled conditions are established for downloading a new control program to replace a control program that a pacemaker has been using. The system enables upgrading pacemakers to new software versions either when desired, or when mandatory; but, it prevents downloading of new program versions to pacemakers which are not permitted to accept the new software. However, the system permits the flexibility of changing the pacemaker to a different type in order to be able to program it with a programmer that does not support the initial pacemaker type.

We claim:

1. A cardiac pacemaker system, said system having an implantable pacemaker and an external programmer, wherein said pacemaker comprises pace means for generating pacing pulses, control means for controlling operation of said pacemaker in accord with a stored device program, first memory means for storing said device program, second memory means for storing device data representative of said implantable pacemaker, and transceiver means for transmitting data to and receiving data from said external programmer; and said external programmer comprises programming means for programming pacemakers, storage means for storing at least a second device program, means for obtaining said device data and determining whether said implantable pacemaker can be programmed by said programmer, option means for presenting an option to download said device with another program when said pacemaker can not be programmed, and downloading means for exercising said option and for downloading said implantable device with said second device program.

2. The system as described in claim 1, wherein said external programmer comprises device data means for storing data representative of a plurality of device programs with each said program rated in accordance with a predetermined hierarchy, and wherein said downloading means permits downloading of said second device program to said implantable pacemaker when it is of a lower rating than the device program that had been stored in said pacemaker.

3. The system as described in claim 1, wherein said second memory means comprises group means for storing data representing a group of pacemaker types, each respective type in said group corresponding to a respective said device program, and type means for storing permission data representative of types corresponding to device programs which said implantable pacemaker is permitted to use.

4. The system as described in claim 3, wherein said external programmer comprises program storage means for storing a plurality of respective device programs, and restricting means for restricting which of said device programs can be downloaded to said implantable pacemaker based on said permission data.

5. The system as described in claim 4, wherein said program storage means stores a plurality of device programs corresponding to different groups, and wherein said restricting means enables downloading of only device programs corresponding to device types of the group of said implantable pacemaker.

6. A method of changing a control program stored in an implanted medical device, comprising:

storing in said device permission data representative of a set of permitted control programs;

using an external programmer having the capacity of downloading to said device a control program;

interrogating said device with said external programmer to obtain said permission data, and determining therefrom said set of permitted control programs; comparing said selected control program with said determined set of control programs; and downloading said selected control program to said device only when it is included in said set.

7. The method as described in claim 6, wherein said programmer has means for ranking the respective control programs of said set in a hierarchy, and enabling means for enabling changing the control program of said device only when said change is an upgrade in terms of said ranking.

8. The method as described in claim 6, comprising downloading changed permission data to said device, thereby changing the set of control programs that can be downloaded to said device.

9. The method as described in claim 6, comprising interrogating said device to determine the control program it is using, storing an upgrade control program in said programmer for upgrading a device which is using a predetermined program, and automatically downloading said upgrade control program to said device when it is determined to be using said predetermined program.

10. A system for controlled changing of a control program stored in an implantable pacemaker, comprising:

an implantable pacemaker, said pacemaker having stimulus means for generating stimulus pulses, control means for controlling the operation of said pacemaker, said control means comprising memory for storing a device program and processor means for carrying out pacemaker functions in accord with said program, set means for storing permission data representing a set of respective device programs which said pacemaker is permitted to use, and device transceiver means for receiving program changes from an external programmer, and for transmitting data representative of said device permission set to said external programmer; and an external programmer having memory means for storing at least one device program, programmer transceiver means for transmitting data to and receiving data from a said implanted pacemaker, determining means for obtaining said permission data and for determining from said permission data whether said at least one device program is permitted for use by said pacemaker, and downloading means for downloading said at least one program to said implantable pacemaker.

11. The system as described in claim 10, wherein said external programmer comprises memory means for storing a plurality of device programs, each of said plurality of programs being associated within a respective set of programs.

12. The system as described in claim 10, wherein said programmer has permission change means for changing the permitted device set of an implanted pacemaker as a function of the permission data obtained from a said pacemaker.

13. The system as described in claim 10, wherein said permission data represents a grade hierarchy of permitted programs, whereby each of said programs is ranked in grade with respect to the other programs in the set.

14. The system as described in claim 13, wherein said downloading means comprises display means for displaying a message before enabling downloading of a program which is a downgrading of rank of the stored program.

15. The system as described in claim 14, wherein said external programmer comprises means for determining when a pacemaker is to be upgraded to another program, and wherein said downloading means comprises automatic upgrading means for upgrading the device program in an implanted pacemaker when an upgrading determination is made.

16. The system as described in claim 10, wherein said set means comprises a stored bit of data corresponding to each possible device program.

* * * * *

UNITED STATES PATENT AND TRADEMARK OFFICE
CERTIFICATE OF CORRECTION

PATENT NO. : 5,843,138
DATED : December 1, 1998
INVENTOR(S) : Xander Evers et al.

It is certified that error appears in the above-indentified patent and that said Letters Patent is hereby corrected as shown below:

Col 7, line 24, delete "48"

Signed and Sealed this

Sixteenth Day of March, 1999

Attest:

Q. TODD DICKINSON

Attesting Officer      Acting Commissioner of Patents and Trademarks